United States Patent [19]

McDaniel

[11] Patent Number: 5,952,372
[45] Date of Patent: Sep. 14, 1999

[54] METHOD FOR TREATING ROSACEA USING ORAL OR TOPICAL IVERMECTIN

[76] Inventor: William Robert McDaniel, 1612 Clearview Dr., Brentwood, Tenn. 37027

[21] Appl. No.: 09/156,280

[22] Filed: Sep. 17, 1998

[51] Int. Cl.$^6$ .................................................. A61K 31/35
[52] U.S. Cl. ........................................... 514/453; 514/859
[58] Field of Search ...................................... 514/859, 453

[56] References Cited

PUBLICATIONS

Izumitani et al. (AN 930376696 JCICST–EPlus, Shodobutsu Rinsho (Japanese Journal of Small Animals Practice), (1993), vol. 12, No. 2, pp. 83–88, Journal code: F0719C(Fig. 7, Tbl. 6, Ref. 2). ISSN: 0286–9616, 1993.

Kamboj et al. (AN 93:385369, BIOSIS, Indian Vet. J., 70 (1), (1993), pp. 61–64).

*Primary Examiner*—Jose' G. Dees
*Assistant Examiner*—Sabiha Qazi

[57] ABSTRACT

A method of treating rosacea in humans involving orally-administered or topically-applied ivermectin is disclosed. More specifically, oral ivermectin in a regimen of 200 micrograms per kilogram body weight per dose for 2 or 3 consecutive doses at least 3 and not more than 7 days apart as the preferred regimen or, alternatively, topical ivermectin compounded to a 2% concentration by weight in a cream, lotion, or gel carrier vehicle is administered as an effective treatment for all clinical stages and signs of rosacea in affected persons.

9 Claims, No Drawings

METHOD FOR TREATING ROSACEA USING ORAL OR TOPICAL IVERMECTIN

BACKGROUND OF THE INVENTION

This invention relates to a method for treatment of rosacea (acne rosacea) in humans employing orally-administered or topically-applied ivermectin. By reducing or eliminating *Demodex folliculorum* organisms from affected skin areas, this method reduces clinical signs of rosacea which are primarily due to allergic and vasomotor responses of the body to the organism in susceptible persons.

Rosacea, originally termed acne rosacea, is a chronic inflammatory skin condition affecting the face and eyelids of certain middle-aged adults. Clinical signs include erythema (redness), dryness, papules, pustules, and nodules either singly or in combination in the involved skin areas. Eyelid involvement may be manifested by mild conjunctival irritation or inflammation of the meibomian (oil) glands on the eyelid margin. Chronic eyelid irritation can result in loss of eyelashes. No visual impairment accompanies the eyelid irritation. Chronic involvement of the nose with rosacea in men can cause a bulbous enlargement known as rhinophyma. In the classic situation, the condition develops in adults between the ages of 30 and 50. While certain lesions of rosacea may mimic lesions of acne vulgaris, the processes are separate and distinct, the principal differences being the presence of comedones (whiteheads and blackheads) only in acne vulgaris and not in rosacea, the characteristic midfacial localization and flushing of rosacea not seen in acne, and the potential for eyelid involvement in rosacea which never occurs in acne. In fact, the clinical observation has been made that persons who have classic acne vulgaris as teenagers rarely, if ever, develop full-blown rosacea as adults.

The etiology of rosacea has been a frequently-discussed topic in medical circles but little consensus has ever been reached. The prominent presence of erythema (redness) and flushing of the face of affected persons with aggravation from heat, sunshine, and alcohol has focused attention on this aspect of the disease. However, treatment with medications to block such vasomotor flushing have no effect on other aspects of the disease such as papules and pustules. Treatment with oral antibiotics has been shown to effectively block progression of rosacea through a poorly-understood anti-inflammatory mechanism, but studies have shown that thee medications do not act by killing either bacteria or *Demodex folliculorum* organisms in affected skin. Reaction to the presence or metabolic activity of Demodex mites in facial follicles has been discussed as a cause of rosacea, but previous studies where topical miticides have been used have shown inconsistent and marginal results. Dietary avoidance of spicy foods and alcohol which cause flushing provides at most temporary symptomatic relief from rosacea. An excellent review of current knowledge in treating rosacea was written by Jansen and Plewig in their chapter titled "Rosacea" in *Clinical Dermatology* (Philadelphia: Lippincott-Raven Publishers, 1997; chapter 10-7.)

Ivermectin (22,23-dihydroavermectin B1) is a safe and effective orally-administered antiparasitic drug that paralyzes and kills treated organisms by increasing cell permeability to chloride ions which in turn overpolarizes nerve and muscle cells. It is a broad-spectrum member of a family of lactone antibiotics known as avermectins which are produced by cultures of the bacterium *Streptomyces avermitilis*. It has been used orally in animals and humans to prevent and treat a variety of parasites including *Strongyloides stercoralis* and *Onchocerca volvulus*. Campbell wrote an informative review of the use of ivermectin in human parasitic diseases ("Ivermectin as an Antiparasitic Agent for Use in Humans," *Annual Review of Microbiology*. 1991. 45: 445–74.) Studies have shown effectiveness in treating human infections with *Sarcoptes scabei* and head lice. *Demodex folliculorum* could logically be expected to be killed by ivermectin also since it, like *Sarcoptes scabei*, is classified among the members of the mite family. Related art specifying products or methods for treating rosacea has not claimed that any beneficial effects of the disclosed agents had anything to do with elimination of *Demodex folliculorum* from the skin of affected individuals. In U.S. Pat. No. 5,654,013, Taylor and Bass disclosed a method of reducing inflammation in rosacea involving lightly rubbing a block of crystalline sodium chloride over moistened skin in affected areas. No claim was made for any antibiotic effect on bacteria or ectoparasites in the skin. In U.S. Pat. No. 3,867,522, Kligman discloses the abrasive use of sodium chloride crystals rubbed over affected skin in acne and related disorders, again with no intended antibiotic effect and with the goal of treatment being the lessening of the severity of the disease and not a permanent or even a temporary cure.

BRIEF SUMMARY OF THE INVENTION

The current invention involves treating rosacea by the oral or topical use of ivermectin. By effectively reducing or eliminating the population of Demodex mites in affected skin areas, this treatment achieves a more complete remission of clinical signs and symptoms of the disease than any previously described method.

DETAILED DESCRIPTION OF THE INVENTION

In the preferred embodiment of this invention, ivermectin is administered orally to a patient with active rosacea in a dose of about 200 micrograms per kilogram of body weight per dose. Because the target organism, *Demodex folliculorum*, is an ectoparasite in the mite family, an effective treatment must be capable of eradicating the entire life cycle of such a microscopic insect, including egg, larval, and adult stages. For this reason, this embodiment treats such rosacea patients with at least two doses timed so that between three and seven days separate the doses. Such spacing allows time for Demodex eggs to hatch into immature mites that are killed before they can mature into egg-producing adults. While two doses has been demonstrated to be quite effective, in unusual cases where absorption is impaired, as many as four doses at three- to seven-day intervals could be employed. After ivermectin carries out its miticidal activity on skin *Demodex folliculorum* organisms, inflammatory responses to them begin to diminish but remnants of the dead mites still elicit some flushing and lesion formation until the cleanup processes of the body remove them, a process requiring six to eight weeks. During this initial phase of ivermectin administration, conventional anti-rosacea medications such as oral tetracycline and topical metronidazole can be employed to suppress early flare-ups and to give early clinical response. No such medications are needed to treat manifestations of rosacea after six to eight weeks have elapsed. After prolonged intevals of freedom from rosacea symptoms, should classic signs begin to reappear, treatment can be repeated. Such retreatments should not be necessary more than one or two times per year.

In an alternative embodiment, ivermectin is formulated into a cosmetically-acceptable topical lotion, cream, or gel and applied to skin affected by rosacea. Because of the well-known barrier effect the skin presents to the penetration of topical medications, such a route of treatment with ivermectin would be anticipated to require once- or twice-daily applications for as long as four weeks to achieve sufficient follicle penetration and effective miticidal activity. A topical formulation that could achieve this effect would contain about 1–5% ivermectin and could be enhanced in penetration if the active agent were encapsulated inside microliposomes. Such a topical treatment would likely need to be repeated more frequently than the preferred oral embodiment, but a disease-free interval should be achieved by each course of therapy.

EXAMPLES

Three adult rosacea patients with varied clinical presentations and with varied disease durations are selected to illustrate the disclosed invention. These patients' cases illustrate the effectiveness of ivermectin treatment on the different clinical manifestations of the disease.

Patient 1

This 44-year old Caucasian female had exhibited clinical evidence of rosacea for 1–2 years and had been treated with limited success with oral tetracycline, topical and oral metronidazole, and cortisone creams. Her facial skin exhibited mid-facial erythema and flushing with papule and pustule formation. In addition, her eyelids exhibited chronic blepharitis and repeated loss of eyelashes, which is quite typical of rosacea. She was treated with ivermectin, 200 micrograms per kilogram of body weight in each of two oral doses with an interval of four days between doses. Oral tetracycline was continued at a dose of 500 milligrams per day for the first 30 days after ivermectin was given and then was discontinued. After a mild initial flareup of mid-facial papules, the condition improved rapidly to the point that by 60 days no papules were present, all eyelashes were growing back, and she had no more flushing with heat or spicy foods. Symptoms had not returned after three months.

Patient 2

This 33-year old Caucasian female had the acute onset of papular and pustular rosacea involving nearly all of her cheeks and chin two months prior to her evaluation. Marked itching and redness were present, but no eye symptoms were noted. Ivermectin in two 200 microgram per kilogram oral doses given three days apart was administered along with a four-week course of oral tetracycline. The clinical signs abated quickly, with itching being gone after one week and papular lesions clearing by three weeks. At two months from the onset of treatment and one month after cessation of tetracycline, no clinical signs or symptoms of rosacea remained.

Patient 3

This 65-year old African-American female had suffered from severe papular and pustular rosacea of the mid-face and nose for 15 years. Tetracycline, in doses of 500–1000 mg per day had proven to be the only partially-effective medication for her. Oral ivermectin was administered in two 200 microgram per kilogram doses given four days apart and tetracycline was continued for one month in a dose of 500 mg per day. Followup at three months from the start of ivermectin therapy revealed only mild hyper-pigmentation at the sites of previous inflamed papules and pustules. The patient reported that no new lesions had been noted for six weeks prior to that 3-month evaluation.

While these examples illustrate the preferred embodiment of this invention, the treatment of rosacea using oral ivermectin, exposure of Demodex mites to ivermectin from any route of administration will result in the elimination of the organisms and secondary amelioration of the signs of inflammation that are typical of rosacea. Therefore, the topical use of ivermectin in any vehicle that allows it to adequately penetrate into skin follicles to reach the level occupied by *Demodex folliculorum* will be an effective treatment for rosacea and is considered to be entirely within the scope of this invention. Changes of dosages, dosing schedules, concentrations, vehicles, and frequency of repetition of ivermectin regimens are also not considered to be outside the scope of this invention.

What is claimed is:

1. A method of treating rosacea by orally-administering or topically-applying ivermectin in a dosage sufficient to fill and eliminate *Demodex folliculorum* mites from hair follicles in affected skin, resulting in cessation of the manifestations of allergic and vasomotor responses to the organism that cause the symptoms and signs of rosacea.

2. The method of claim 1, wherein one oral dose of ivermectin is about 200 micrograms per kilogram of body weight.

3. The method of claim 1, wherein said doses of oral ivermectin are repeated about two to four times with spacing of three to seven days between them.

4. The method of claim 1, wherein said rosacea affects facial skin or eyelids, or both.

5. The method of claim 1, wherein said topically-applied ivermectin is formulated in a carrier lotion, cream, or gel.

6. The method of claim 5, wherein the concentration of ivermectin in said topically-applied lotion, cream, or gel is about one to five percent by weight.

7. The method of claim 5, wherein said topically-applied ivermectin is applied to affected skin areas but not to eyelids.

8. The method of claim 5, wherein said topically-applied ivermectin is applied to affected skin areas at least once and not more than twice daily for a period of about two to four weeks.

9. The method of claim 5, wherein said topically-applied ivermectin is encapsulated inside microliposomes before being formulated into said carrier lotion, cream, or gel.

* * * * *